US008062854B2

(12) United States Patent
Schmidt et al.

(10) Patent No.: US 8,062,854 B2
(45) Date of Patent: Nov. 22, 2011

(54) METHOD FOR ENRICHING A PROKARYOTIC DNA

(75) Inventors: Karl-Hermann Schmidt, Stadtroda (DE); Eberhard Straube, Jena (DE); Stefan Russwurm, Jena (DE)

(73) Assignee: SIRS-Lab GmbH, Jena (DE)

( * ) Notice: Subject to any disclaimer, the term of this patent is extended or adjusted under 35 U.S.C. 154(b) by 1325 days.

(21) Appl. No.: 10/528,235

(22) PCT Filed: Aug. 8, 2003

(86) PCT No.: PCT/EP03/08825
§ 371 (c)(1),
(2), (4) Date: Jul. 30, 2008

(87) PCT Pub. No.: WO2004/033683
PCT Pub. Date: Apr. 22, 2004

(65) Prior Publication Data
US 2010/0316993 A1 Dec. 16, 2010

(30) Foreign Application Priority Data
Sep. 18, 2002 (EP) .................................... 02020904

(51) Int. Cl.
G01N 33/53 (2006.01)
G01N 31/00 (2006.01)

(52) U.S. Cl. ............ 435/7.21; 435/7.1; 436/1; 436/501; 436/518; 424/9.1; 424/520; 422/50; 530/300; 530/350

(58) Field of Classification Search .......................... None
See application file for complete search history.

(56) References Cited

U.S. PATENT DOCUMENTS

| 5,817,290 | A | 10/1998 | Vijg et al. |
| 6,239,116 | B1 | 5/2001 | Krieg et al. |
| 7,507,872 | B2 | 3/2009 | Akira et al. |
| 2003/0124655 | A1 | 7/2003 | Akira et al. |
| 2008/0003568 | A1 | 1/2008 | Schmidt et al. |
| 2008/0076671 | A1 | 3/2008 | Bird et al. |

FOREIGN PATENT DOCUMENTS

| CA | 2498951 | 4/2004 |
| CA | 2 385 302 | 8/2009 |
| JP | 2002-034565 | 2/2002 |
| WO | WO 01/12659 | 2/2001 |
| WO | WO 02/06482 | 7/2003 |

OTHER PUBLICATIONS

Chinese Office Action, Chinese Application No. 03822233.7, 8 pages, Sep. 26, 2008 added LVC Jun. 24, 2011.
English Translation of Chinese Office Action, Chinese Application No. 03822233.7, 8 pages, Oct. 21, 2008 added LVC Jun. 24, 2011.
Sequence from GenBank Accession No. AB045180, Apr. 14, 2005 added LVC Jun. 24, 2011.
International Search Report for International Application No. PCT/EP2005/002198 dated mailed Sep. 28, 2005.
Stacey, et al., The Molecular Basis for the Lack of Immunostimulatory Activity of Vertebrate DNA, The Journal of Immunology, 70:3614-3620 (2003).
Rothenfuber, et al., CpG-Oligonukleotide: Immuntherapie nach dem Muster bakterieller DNA, Deutsches Arzteblatt 98, Heft 15 vom Apr. 13, 2001, pp. A981-A985 (2001).
S. Sachse et al., "Using a DNA-binding protein to enrich prokaryotic DNA from a mixture of both, eukarytoic and prokaryotic DNA," 56, DGHM-Jahrestagung, XP002332325. Sep. 29, 2004.
NCBI Sequence Database, AAF37799, Dec. 8, 2004 added LVC on Jun. 24, 2011.
International Journal of Medical Microbiology, 294S1, p. 181, 56. Jahrestagungder DGHN (Sep. 26-29, 2004).
Clinical Microbiology and Infection, 15th European Congress of Clinical Microbiology and Infectious Diseases, vol. 11, Supplement 2, p. 67. Apr. 2-5, 2005.
Application and File History for U.S. Appl. No. 10/591,633, filed Jul. 17, 2007, inventor Schmidt et al., at www.uspto.gov.
Hacker, Georg, Redecker, Vanessa, and Hacker, Hans. (2002) Activation of the Immune System by Bacterial CpG-DNA. Immunology 105:245-251.
Voo, Kui Shin, Diana L Carlone, Britta M. Jacobsen, Anna Flodin, and David G. Skalnik. (2000) Cloning of a Mammalian Transcriptional Activator That Binds Unmethylated CpG Motifs and Shares a CXXC Domain with DNA Methyltransferase, Human Trithorax, and Methyl-CpG Binding Domain Protein 1. Molecular and Collular Biology, 20(6):2108-2121.
Cross et al., "Purification of CpG islands using a methylated DNA binding column," Nature Genetics, New York, NY, vol. 6, No. 3, Mar. 1, 1994, pp. 236-244, XP 000578157.
Carlone et al., "Cloning and characterization of the gene encoding the mouse homologue of CpG binding protein," Gene: an International Journal on Genes and Genomes, Elsevier Science Publishers, Barking, GB, vol. 295, No. 1, Jul. 24, 2002, pp. 71-77, XP 004381373.
Hemmi et al., "A Toll-like receptor recognizes bacterial DNA," Nature, MacMillan Journals Ltd., London, GB, vol. 408, No. 6813, Dec. 7, 2000, pp. 740-745, XP 002168474.

*Primary Examiner* — Lisa Cook
(74) *Attorney, Agent, or Firm* — Patterson Thuente Christensen Pederson, P.A.

(57) ABSTRACT

A method is described for enriching procaryotic DNA, said method including the steps of contacting at least one procaryotic DNA with at least one protein or polypeptide which is capable of specifically binding to non-methylated CpG motifs, and separating the protein/polypeptide-DNA complex. Moreover, the application relates to a kit for carrying out said method.

19 Claims, 2 Drawing Sheets

METHOD FOR ENRICHING A PROKARYOTIC DNA

RELATED APPLICATION

This application claims priority to PCT Application No. PCT/EP2003/008825 filed 8 Aug. 2003 and European Application No. 02020904.5 filed 18 Sep. 2002.

TECHNICAL FIELD OF THE INVENTION

The invention relates to a method of enriching procaryotic DNA as well as to a kit for carrying out said method.

BACKGROUND OF THE INVENTION

Infections caused by bacteria are one of the most frequent causes of inflammatory diseases. For the prognosis of the clinical course as well as, in particular, for timely selection of suitable therapeutic measures, early detection of the bacterial pathogens is of decisive importance.

SUMMARY AND DETAILED DESCRIPTION

In the detection of bacterial pathogens, use is made, above all, of different methods of cultivating cells. However, methods of molecular biology which are based on the detection of pathogen-specific nucleic acids have also become more important recently. In addition to the high specificity of these methods, mention must be made of the little time required as an essential advantage over conventional methods. However, the sensitivity of the detection of procaryotic DNA directly from body fluids and from test material that has not been pre-treated has hitherto been much too low as compared to the culture of microorganisms. An amount of nucleic acids of bacteria sufficient to detect pathogens directly from the test material that has not been pre-treated is achieved, if at all, in the region of the 16S-mRNA molecules. However, this requires that the bacteria to be detected be present in the metabolic phases and express sufficient 16S-mRNA.

This is usually not the case, in particular in patients who are subject to antibiotic therapy. Moreover, certain pathogenicity factors of bacteria are not expressed every time, although the corresponding genes are present in the bacterial genome. Therefore, the detection of the pathogenicity factors and resistance of bacteria at the chromosomal level is indispensable for the diagnosis of septic disease states.

This applies even more because, at this level, a distinction can also be made between pathogenic and commensal bacteria.

Most frequently, the detection of pathogen-specific nucleic acids is effected by amplification of the procaryotic DNA by means of the polymerase chain reaction (PCR) or the ligase chain reaction (LCR), respectively. The high specificity and fast availability of the results is contrasted by the susceptibility to interference or by strongly inhibiting factors of clinical samples.

In a conventional PCR detection method, successful detection of pathogens in the blood requires isolation of total DNA from at least 1 to 5 ml of blood. However, the total DNA concentration is then too high to be employed directly in a PCR reaction.

Things are different with regard to the blood culture for detection of sepsis pathogens. In this case, the lower detection limit is less than 10 bacteria per ml. This detection limit is presently achieved only by PCR protocols whose target sequence is in the 16S-RNA region and which are therefore dependent on the expression of said target sequence. Greater diagnostic reliability can be expected of PCR protocols which have their target sequences in the chromosome of the microorganisms. The expression behavior of different genes can be considerably changed or limited, especially under the influence of an ongoing antibiotic therapy, even if the antibiotic used is ultimately not effective. This situation is often found particularly in intensive therapy wards, where most patients receive antibiotic treatment, thus not allowing to grow any relevant bacteria from blood cultures or other samples for this reason.

Due to insufficient sensitivity, the detection of pathogen-specific nucleic acids, without an amplification step by direct detection of procaryotic DNA (probe technique, FISH technique), is of diagnostic importance only at a sufficiently high germ number in the test material.

The essential problems of the detection of procaryotic DNA for identification of bacterial pathogens in body fluids consist, beside PCR-inhibiting ingredients in the test material, mainly in the excess of eucaryotic DNA versus procaryotic DNA. In this connection, competitive processes in DNA analysis as well as the low quantity of procaryotic DNA can be regarded as a hindrance to a qualitative and quantitative detection of pathogens.

The usual methods of DNA isolation enrich the total DNA of a body fluid so that the ratio of host DNA to microbial DNA may be between $1:10^{-6}$ and $1:10^{-8}$. This difference makes the difficulty in detecting microbial DNA in body fluids quite clear.

Therefore, it is an object of the present invention to provide a method of isolating and/or enriching microbial DNA, in test samples having a high content of eucaryotic DNA from patients with infections, for quick and easy detection of pathogens, said detection enabling early diagnosis of infections caused by bacterial pathogens.

According to the invention, this object is achieved by a method of enriching procaryotic DNA, comprising the steps of a) contacting at least one procaryotic DNA in solution with at least one protein or polypeptide which is capable of specifically binding to procaryotic DNA, thus forming a protein or polypeptide DNA complex, and b) separating said complex.

In this case, the term procaryotic DNA relates to both viral and bacterial DNA. Said DNA may be purified and dissolved again or may be present directly in the original source (e.g. body fluid, such as blood, serum, etc.).

Separation may be effected by means of different methods of isolating or enriching DNA protein complexes or DNA polypeptide complexes that are well-known to the person skilled in the art. In doing so, use will be made preferably of methods in which the DNA-binding protein is immobilized to a carrier matrix in order to enrich the DNA from the sample solution.

According to a preferred embodiment, the separation is followed by a step of separating the DNA and the protein/polypeptide. This may be effected, for example, by conventional methods of DNA purification which are known to the person skilled in the art. In the most simple case, the separation is based on the change in pH value or in the salt concentration (e.g. to 1 M NaCl) of the medium/buffer or on the addition of chaotropic reagents, etc.; i.e. suitable parameters which lead to the separation of the protein-DNA-complex. Such methods are known to the person skilled in the art.

According to a further preferred embodiment, the protein or the polypeptide is coupled to a carrier. This embodiment represents a particularly simple way of enriching procaryotic DNA, because the separation from the solution is particularly easy, for example by means of physical removal (e.g. by centrifugation) of the charged carrier(s) from the solution.

As the solution of the procaryotic DNA, any suitable solvent is basically suitable. However, the method is particularly useful for enriching procaryotic DNA from solutions which contain different biomolecular species, in particular different types of DNA. The invention preferably relates to a method of separating and enriching procaryotic or viral DNA and eucaryotic DNA from a mixture of procaryotic or viral DNA. In doing so, for example, the procaryotic DNA which is present in body fluids is separated from the eucaryotic DNA, by specific binding to the protein or to the polypeptide, and enriched. The procaryotic DNA enriched in this way facilitates detection of procaryotic pathogens with the help of molecular biology methods and can contribute to the diagnosis of diseases caused by pathogenic pathogens.

In particular, the embodiment according to which the DNA-binding protein or polypeptide is immobilized to the surface of a carrier is suitable for adsorption of procaryotic DNA from body fluids, preferably from blood. Moreover, this approach allows removal of microbial DNA, which is present in blood or other body fluids, from said fluids. The body fluid (e.g. whole blood, serum or liquor) purified in this way from the microbial DNA, which is also capable in itself of initiating severe inflammatory reactions in patients, can then be fed back into the body.

Body fluids in the sense of the invention are understood to be all fluids originating from the body of a mammal, including humans, in which disease pathogens may occur, such as blood, urine, liquor, pleural, pericardial, peritoneal as well as synovial fluids. The description of the invention referring to human blood is not to be construed as limitative, but only as an exemplary application.

Proteins or polypeptides in the sense of the invention are understood to be all eucaryotic and procaryotic proteins which are capable of specifically binding procaryotic DNA. Proteins or polypeptides which are capable of specifically binding non-methylated CpG-motifs are particularly suitable for this purpose.

Bacterial pathogens are preferably understood to be pathogens of sepsis, but also any other bacterial pathogens of infections. They may differ from commensal pathogens, which are sometimes also found in test samples from patients, but do not have any pathogenic significance.

In isolating the total DNA from infected body liquids, the ratio of host-DNA to pathogen-DNA may be, in many cases, $1:10^{-6}$ to $1:10^{-8}$ and less. Through the specific binding of procaryotic DNA to the protein or polypeptide having such selective properties, the method according to the invention enables enrichment by 3 exponential units and more.

The protein or the polypeptide may be coupled directly or indirectly to the carrier. The type of coupling depends on the carrier and the carrier material. Suitable carriers include, in particular, membranes, microparticles and resins, or similar materials for affinity matrices. Suitable materials for binding of the protein or of the polypeptide, as well as—depending on the type of material—for carrying out such binding, are well-known to the person skilled in the art. For indirect coupling, such specific antibodies against the protein or polypeptide are suitable, for example, which are in turn bound to the carrier by known methods.

One application of the method according to the invention consists in enriching procaryotic DNA. A further application consists in the separation of procaryotic DNA from a mixture of eucaryotic and procaryotic DNA by binding of the procaryotic DNA to a specific protein or polypeptide which has been immobilized to a matrix. The mixture of the body's own DNA and procaryotic DNA is contacted with the affinity matrix by means of suitable methods and, in doing so, the procaryotic DNA is bound to the immobilized protein; the eucaryotic DNA passes, for example, through a separating column and may be collected separately. Affinity matrices may be, for example, polymeric polysaccharides, such as agaroses, other biopolymers, synthetic polymers, or carriers having a silicate backbone, such as porous glasses or other solid or flexible carriers on which the DNA-binding protein or polypeptide is immobilized. After separation of procaryotic DNA from eucaryotic DNA has been effected, the affinity matrix is rinsed with a suitable reagent, so that either the binding protein with the coupled procaryotic DNA is separated from the matrix and/or the procaryotic DNA is separated from the binding protein and is available for further process steps in a sufficient amount.

A further application of the method according to the invention consists in the separation and enrichment of procaryotic DNA from eucaryotic DNA by binding of the procaryotic DNA to a specific protein which has been immobilized on microparticles. In this connection, all microparticles which allow the DNA-binding protein or polypeptide to be immobilized are suitable. Such microparticles may consist of latex, plastics (e.g. styrofoam, polymer), metal or ferromagnetic substances. Furthermore, use may also be made of fluorescent microparticles, such as those available from the Luminex company, for example. After the procaryotic DNA has been bound to the proteins immobilized on microparticles, said microparticles are separated from the mixture of substances by suitable methods, such as filtration, centrifugation, precipitation, sorting by measuring the intensity of fluorescence, or by magnetic methods. After separation from the microparticles, the procaryotic DNA is available for further processing.

Another application of the method according to the invention consists in the separation and enrichment of procaryotic DNA from eucaryotic DNA by binding of the procaryotic DNA to a specific protein or polypeptide, which is subsequently separated from other ingredients of the mixture by electrophoresis.

A further application of the method according to the invention consists in the separation and enrichment of procaryotic DNA from eucaryotic DNA by binding of the procaryotic DNA to the protein or polypeptide. Said protein is subsequently bound to corresponding antibodies. The antibodies may be bound to solid or flexible substrates, such as glass, plastics, silicon, microparticles, membranes, or may be present in solution. After binding of the procaryotic DNA to the protein or the polypeptide and binding of the latter to the specific antibody, separation from the substance mixture is effected by methods known to the person skilled in the art.

As protein or polypeptide, any protein or polypeptide is particularly suitable which binds procaryotic DNA with non-methylated CpG motifs, for example. For this purpose, specific antibodies or antisera against procaryotic DNA are suitable, for example. Their preparation and isolation are known to the person skilled in the art.

Procaryotic DNA differs from eucaryotic DNA, for example, by the presence of non-methylated CpG motifs. Thus, the protein/polypeptide is conveniently a protein which specifically recognizes and binds non-methylated CpG motifs. Conveniently, this also includes a specific antibody or a corresponding antiserum. According to a further preferred embodiment, the protein or polypeptide is a protein or polypeptide encoded by the TLR9 gene or by the CGBP gene.

This embodiment of the invention is based on the finding that eucaryotic DNA and procaryotic DNA differ in their content of CpG motifs. In the procaryotic DNA, cytosine-guanosine-dinucleotides (CpG motifs) are present in an excess of 20 times that of eucaryotic DNA. In procaryotic DNA, these motifs are non-methylated, whereas they are methylated for the most part in eucaryotic DNA, which further enhances the difference. Non-methylated CpG motifs are non-methylated deoxycytidylate-deoxyguanylate-dinucleotides within the procaryotic genome or within fragments thereof.

Secondly, this preferred embodiment of the invention is based on the finding that there are proteins or polypeptides which bind specifically to non-methylated CpG motifs of the DNA. The binding property of these proteins/polypeptides is used, according to the invention, in order to bind procaryotic DNA, on the one hand, and thus to enrich it, on the other hand, from a sample mostly containing eucaryotic DNA.

An application for isolating cDNA, which uses the presence of methylated CpG motifs in eucaryotic DNA was described by Cross et al. Nature Genetics 6 (1994) 236-244. The immunostimulatory application of single-stranded oligodeoxyribonucleotides (ODN) with the corresponding CpG motifs has been shown several times (Häcker et al., Immunology 105 (2002) 245-251, U.S. Pat. No. 6,239,116). As recognition molecules of the procaryotic CpG motifs, two receptor proteins have been identified so far. Toll-like-receptor 9 is known from WO 02/06482 as a molecule recognizing non-methylated CpG motifs. Voo et al. Molecular and Cellular Biology (2000) 2108-2121 describe a further receptor protein, i.e. the human CpG-binding protein (hCGBP), which is used in an analytic approach as a recognition molecule for detecting non-methylated CpG motifs in procaryotic DNA. In both publications, the CpG-binding proteins are not used for isolating or enriching procaryotic DNA.

A protein or polypeptide which is encoded by cDNA having a sequence with a homology of at least 80%, preferably at least 90%, and particularly preferably at least 95%, to the sequence according to gene bank access no.: NM-014593 (SEQ. ID No. 1) (version NM-014593 1, GI:7656974; NCBI database) is particularly suitable. These are proteins or polypeptides which correspond to CGBP or are derived therefrom and which specifically recognize and bind CpG motifs. A method of enriching prokaryotic DNA also comprises a protein or polypeptide which is encoded by cDNA with a sequence having a homology of at least 80%, preferably at least 90%, to the sequence according to gene bank access no.: X14-165661 (SEQ. ID No. 2).

According to a further preferred embodiment, the protein or polypeptide is encoded by cDNA having a sequence with a homology of at least 80%, preferably at least 90%, to the sequence according to gene bank access no. AB045180 (SEQ. ID No. 3) (coding sequence of the TLR9 gene; NCBI database, version AB045180.1; GI: 11761320) or a fragment thereof, preferably cDNA having a homology of at least 80%, particularly preferably 90%, to transcript variant A (gene bank access no. NM-138688 (SEQ. ID No. 4); version NM-017442.1; GI: 20302169; NCBI database) or transcript variant B (gene bank access no. NM-017442 (SEQ. ID No. 5); version W-138688.1; GI: 20302170; NCBI database).

Moreover, the invention relates to a method of purifying body fluids to remove procaryotic DNA. In this connection, it is convenient for the separation to be effected extracorporally, under sterile conditions, to allow the body fluids to be fed back into the body again, so that the body's own immune system is assisted in eliminating infections by removing the procaryotic DNA contained in said body fluids.

Any suitable chemical, mechanical or electrochemical processes may be considered for the extracorporal removal of procaryotic DNA from body fluids. Further, the combination with other extracorporal therapeutic methods, such as hemoperfusion, heart-lung machine or endotoxin absorbers, represents a further convenient application. This enumeration does not represent a limitation of the methods.

According to a particularly preferred embodiment, the invention relates to a method of detecting procaryotic DNA. In this case, the enrichment of the procaryotic DNA is followed by a step of amplifying said procaryotic DNA, for which all common methods of amplification are suitable (PCR, LCR; LM-PCR, etc.).

Moreover, the invention relates to a kit for enriching procaryotic DNA by means of one of the above-described methods, said kit containing at least the protein/polypeptide, preferably further reagents suitable to carry out said method.

According to a preferred embodiment, said kit contains, in addition to the protein/polypeptide, at least one set of primers, which are suitable to amplify genomic DNA of certain procaryonts under standard conditions.

The invention has the advantage that, by specific binding of non-methylated procaryotic DNA rich in CpG motifs to proteins with specific affinity for such structures, procaryotic DNA from the total DNA of an infected host is successfully concentrated and thus the sensitivity of detection of pathogen DNA in body fluids is strongly enhanced.

The possibilities of separating procaryotic DNA from eucaryotic DNA using a specifically binding protein are no more time-consuming than known methods of isolating total DNA. However, the following detection can then be effected only via a PCR reaction. A nested PCR will not be required in most cases, which makes it possible to save a considerable amount of time in diagnostics.

The invention will be explained in more detail below by means of examples, without limiting it thereto.

EXAMPLE 1

Prior Art Method of Detection

Fresh, heparinized human blood, which contains streptococcus pyogenes with 103/ml colony-forming units as pathogens, is used for detection of pathogens. The DNA is isolated by means of absorption to DNA-binding matrix using commercial kits for isolation of total DNA from body fluids according to modified instructions from the manufacturer. For this purpose, 200 μl of the total lysis buffer, which contains proteinase K and SDS, is added to 100 μl of infected blood in Eppendorf tubes. The mixture is incubated at 37° C. for 30 min. and then heated to 95° C. for 20 min. After cooling, 20 μg of mutanolysine are added and incubated at 37° C. for another 60 min. After centrifugation, the supernatant is applied to the centrifugal columns using DNA-binding matrix and the DNA is purified according to the manufacturer's instructions. The purified DNA is placed in a final volume of 100 μl of 0.01 mol tris buffer, pH 7.5, or in an equal amount of elution buffer from the manufacturer. For detection of pathogens, primers are selected to identify the streptolysin O gene (slo).

1. PCR. Amplification of a 465 bp Fragment

Forward primer 1: 5'-AGCATACAAGCAAATTTTTACACCG (SEQ ID No. 6)

Reverse primer 2: 5'-GTTCTGTTATTGACACCCGCAATT (SEQ ID No. 7)

Primer Concentration 1 mg/ml
Starting material: 5 µl isolated DNA
0.5 µl primer fw 1
0.5 µl primer ry 2
14 µl aqua dest
total 25 µl in Ready to go Kit (Amersham-Biosciences)
Reaction:

| | |
|---|---|
| 1x | 5 min 95° C. |
| 40 cycles each at | 30 sec. 95° C. |
| | 30 sec. 51° C. |
| | 3 min 72° C. |
| 1× | 7 min 72° C. |

Figure 1:
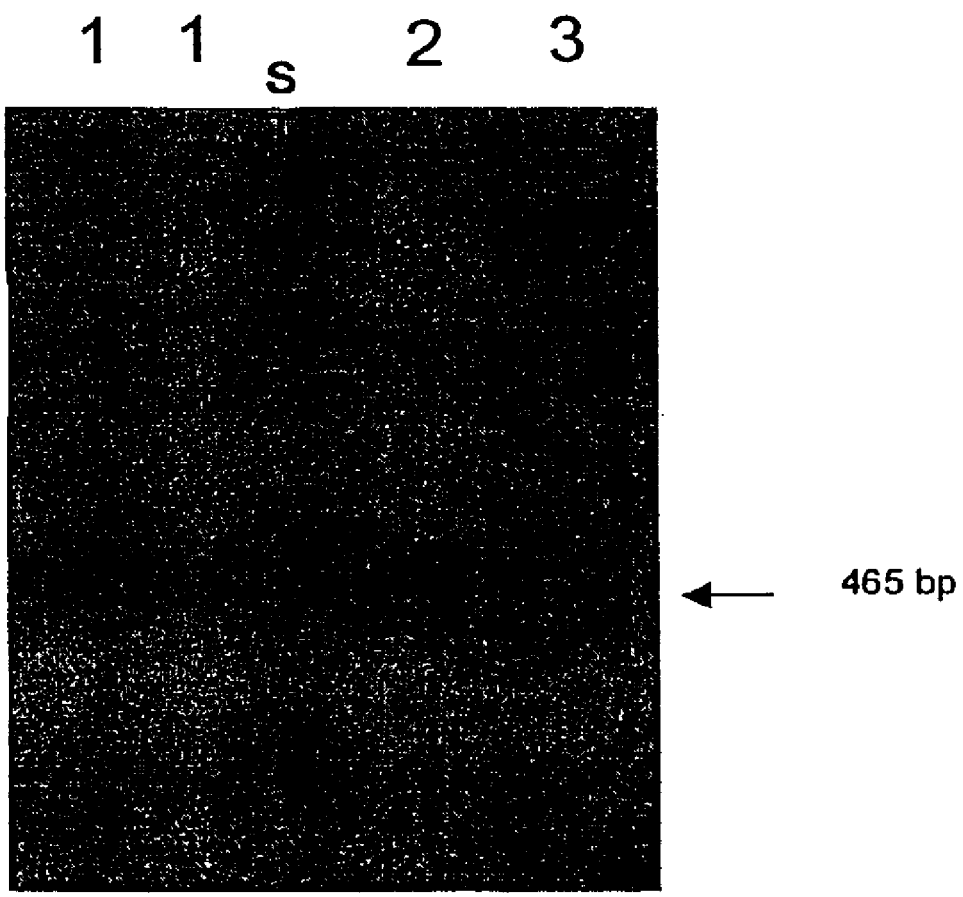
FIG. 1 shows the PCR of *streptococci*-DNA in human blood.

The results of the PCR of streptococci-DNA in human blood are shown in FIG. 1. 10 µl of the 25 µl of starting material were separated. 1) PCR starting material containing 5 µl template DNA; 2) starting material containing 5 µl template, at a dilution of 1:10. 3) positive control: 0.2 µl of streptococci-DNA as template in the absence of eucaryotic DNA from blood. ST) molecular weight standard Result: The primary PCR does not result in a visible PCR product. Therefore, a 2. PCR (nested PCR) was carried out as below.

2. PCR (Nested): Amplification of a 348 by Fragment Contained in the Above Slo-Fragment.

Forward primer 3: 5'-CCTTCCTAATAATCCTGCGGATGT-3' (SEQ ID No. 8)

Reverse primer 4: 5'-CTGAAGGTAGCATTAGTCTTTGATAACG-3' (SEQ ID No. 9)

Primer concentration: 1 mg/ml
Starting material: 5 µl from PCR1, sample 1, FIG. 1
0.5 µl primer fw 1
0.5 µl primer ry 2
14 µl aqua dest
total 25 µl in Ready to go Kit (Amersham-Biosciences)
Reaction:

| | |
|---|---|
| 1x | 5 min 95° C. |
| 50 cycles each at | 30 sec. 95° C. |
| | 30 sec. 54° C. |
| | 3 min 72° C. |
| 1× | 7 min 72° C. |

Figure 2:
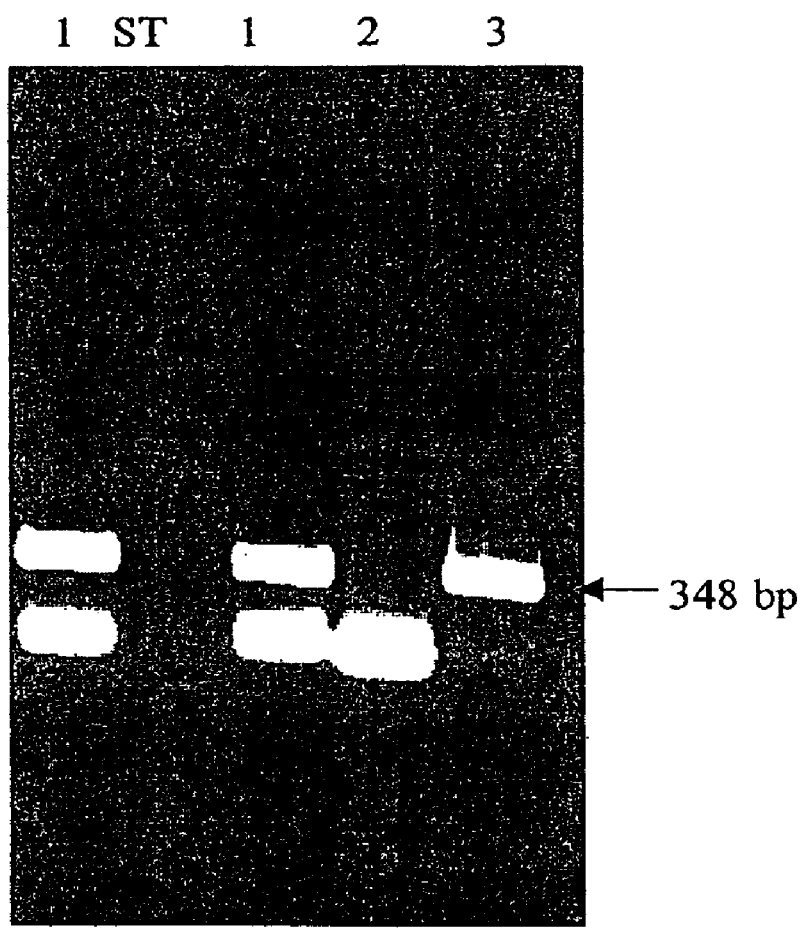
FIG. 2 shows the nested PCR with the PCR products according to FIG. 1.

FIG. 2 shows the nested PCR with the PCR products according to FIG. 1 as template. The samples correspond to those of FIG. 1.

Result: In the nested PCR, the desired slo-DNA fragment is amplified at a pathogen number of 100 *streptococci* cells per 100 µl blood (sample 1). At 5 µl template DNA in the 1$^{st}$ PCR (FIG. 1), this corresponds to about 5 to 10 template molecules. At a dilution of 1:10 (sample 2), sensitivity is exhausted (0.5 to 1 template molecules).

EXAMPLE 2

Carrying Out the Method According to the Invention

The DNA is dissolved from a cell lysate as described above for the previous PCR methods. The difference is that between 1 ml and 5 ml of test material are employed.

Three milliliters of fresh, heparinized or citrate-added human blood, which contains streptococcus pyogenes with 10²/ml colony-forming units as pathogens, is used for detection of pathogens. The DNA is isolated by means of lysis buffers which contain SDS and proteinase K, using commercial kits to isolate total DNA from body fluids according to modified instructions from the manufacturer. For this purpose, 6 ml of the total lysis buffer, which contains proteinase K and SDS, is added to 6 ml of infected blood. The mixture is incubated at 37° C. for 30 min. and then heated to 95° C. for 20 min. After cooling, 200 µg of mutanolysine are added and incubated at 37° C. for another 60 min. After centrifugation, the mixture is precipitated with ethanol at a final concentration of 70%, and upon centrifugation, the pellet is washed with 2 ml of 70% ethanol. The ethanol residue is removed in a vacuum centrifuge and the precipitated DNA is collected in 500 µl TE buffer. The DNA is then applied to a column which contains 0.5 ml of sepharose and is immobilized on the 1 mg of TLR9. The column is washed with 5 volumes of TE buffer. Elution is carried out with chaotropic ions at a high concentration, e.g. with 0.7 ml of a 6 mole NaJ or KSCN solution. This eluate can then be applied directly to a commercial DNA-isolating centrifugal column, and the CpG-enriched DNA may be isolated according to instructions, as in the initial example, to a small volume of between 20 µl and 100 µl and employed for further analysis, such as pathogen PCR.

The invention claimed is:

1. A method of enriching procaryotic DNA, said method comprising:
   a) contacting at least one procaryotic DNA in solution with at least one protein or polypeptide which is capable of specifically binding to the procaryotic DNA, thus forming a protein or polypeptide DNA complex, and
   b) isolating or enriching said complex.

2. The method of claim 1, wherein the isolating or enriching is followed by a step of separating the DNA and the protein or polypeptide.

3. The method of claim 1, wherein the protein or the polypeptide is coupled to a carrier.

4. The method of claim 3, wherein the protein or the polypeptide is coupled directly to said carrier.

5. The method of claim 3, wherein the protein or the polypeptide is coupled to the carrier via an antibody directed against the protein or the polypeptide.

6. The method of claim 3, wherein the carrier is provided as a matrix, as microparticles or as a membrane.

7. The method of claim 1, wherein isolating or enriching is effected by means of an antibody or antiserum directed against the protein or polypeptide.

8. The method of claim 1, wherein the isolating or enriching is effected by means of electrophoresis.

9. The method of claim 1, wherein the protein or the polypeptide is an antibody or antiserum directed against non-methylated CpG motifs.

10. The method of claim 1, wherein the protein or polypeptide is encoded by the TLR9 gene or by the CGBP gene.

11. The method of claim 10, wherein the protein or polypeptide is encoded by a cDNA with a sequence having a homology of at least 80% to SEQ. ID NO. 3 or a fragment thereof, or cDNA having a homology of at least 80% to SEQ. ID NO. 4 or a homology of at least 80% to SEQ. ID NO. 5.

12. The method of claim 1, wherein the solution contains eukaryotic and procaryotic DNA.

13. The method of claim 12, wherein the solution is a body fluid.

14. A method of purifying body fluids from procaryotic DNA comprising
   a) contacting at least one procaryotic DNA from a body fluid with at least one protein or polypeptide which is capable of specifically binding to the procaryotic DNA, thus forming a protein or polypeptide DNA complex, and
   b) separating said complex extracorporally under sterile conditions.

15. A method of detecting procaryotic DNA comprising
   a) contacting at least one procaryotic DNA from a body fluid with at least one protein or polypeptide which is capable of specifically binding to the procaryotic DNA, thus forming a protein or polypeptide DNA complex,
   b) separating said complex, and
   c) amplifying the procaryotic DNA.

16. A kit for detecting or enriching procaryotic DNA comprising at least one protein or polypeptide which is capable of specifically binding to the procaryotic DNA.

17. The kit of claim 16, further comprising one or more sets of PCR primers.

18. The kit of claim 17 further comprising a carrier that is coupled to the at least one protein or polypeptide.

19. The kit of claim 18, wherein the protein or the polypeptide is an antibody or antiserum directed against non-methylated CpG motifs.

* * * * *

SEQUENCE LISTING

<160> NUMBER OF SEQ ID NOS: 9

<210> SEQ ID NO 1
<211> LENGTH: 2444
<212> TYPE: DNA
<213> ORGANISM: Homo sapiens

<400> SEQUENCE: 1

```
agatggcggc gcctgagggg tcttgggggc tctaggccgg ccacctactg gtttgcagcg       60
gagacgacgc atggggcctg cgcaatagga gtacgctgcc tgggaggcgt gactagaagc      120
```

```
ggaagtagtt gtgggcgcct ttgcaaccgc ctgggacgcc gccgagtggt ctgtgcaggt      180
tcgcgggtcg ctggcggggg tcgtgaggga gtgcgccggg agcggagata tggagggaga      240
tggttcagac ccagagcctc cagatgccgg ggaggacagc aagtccgaga tggggagaa       300 tgcgcccatc tactgcatct gccgcaaacc ggacatcaac tgcttcatga tcgggtgtga      360
caactgcaat gagtggttcc atggggactg catccggatc actgagaaga tggccaaggc      420
catccgggag tggtactgtc gggagtgcag agagaaagac cccaagctag agattcgcta      480
tcggcacaag aagtcacggg agcgggatgg caatgagcgg gacagcagtg agccccggga      540
tgagggtgga gggcgcaaga ggcctgtccc tgatccaaac ctgcagcgcc gggcagggtc      600
agggacaggg gttggggcca tgcttgctcg gggctctgct tcgccccaca aatcctctcc      660
gcagcccttg gtggccacac ccagccagca tcaccagcag cagcagcagc agatcaaacg      720
gtcagcccgc atgtgtggtg agtgtgaggc atgtcggcgc actgaggact gtggtcactg      780
tgatttctgt cggacatga agaagttcgg ggccccaac aagatccggc agaagtgccg        840
gctgcgccag tgccagctgc gggcccggga atcgtacaag tacttccctt cctcgctctc      900
accagtgacg ccctcagagt ccctgccaag gccccgccgg ccactgccca ccaacagca       960 gccacagcca tcacagaagt tagggcgcat ccgtgaagat gaggggggcag tggcgtcatc     1020 aacagtcaag gagcctcctg aggctacagc cacacctgag ccactctcag atgaggacct     1080
acctctggat cctgacctgt atcaggactt ctgtgcaggg gcctttgatg caatggcct      1140 gccctggatg agcgacacag aagagtcccc attcctggac cccgcgctgc ggaagagggc     1200
agtgaaagtg aagcatgtga agcgtcggga gaagaagtct gagaagaaga aggaggagcg     1260
atacaagcgg catcggcaga agcagaagca caggaataa tggaaacacc cagagagggc      1320
tgatgccaag gaccctgcgt cactgccccca gtgcctgggg cccggctgtg tgcgccccgc    1380
ccagcccagc tccaagtatt gctcagatga ctgtggcatg aagctggcag ccaaccgcat     1440
ctacgagatc ctcccccagc gcatccagca gtggcagcag agcccttgca ttgctgaaga     1500
gcacggcaag aagctgctcg aacgcattcg ccgagagcag cagagtgccc gcacccgcct     1560
tcaggaaatg gaacgccgat tccatgagct tgaggccatc attctacgtg ccaagcagca     1620
ggctgtgcgc gaggatgagg agagcaacga gggtgacagt gatgacacag acctgcagat     1680
cttctgtgtt tcctgtgggc accccatcaa cccacgtgtt gccttgcgcc acatggagcg     1740
ctgctacgcc aagtatgaga gccagacgtc ctttgggtcc atgtacccca cacgcattga     1800
aggggccaca cgactcttct gtgatgtgta taatcctcag agcaaaaacat actgtaagcg     1860 gctccaggtg ctgtgccccg agcactcacg ggaccccaaa gtgccagctg acgaggtatg     1920
cgggtgcccc cttgtacgtg atgtctttga gctcacgggt gacttctgcc gcctgcccaa     1980
gcgccagtgc aatcgccatt actgctggga gaagctgcgg cgtgcggaag tggacttgga     2040
gcgcgtgcgt gtgtggtaca agctggacga gctgtttgag caggagcgca atgtgcgcac     2100
agccatgaca aaccgcgcgg gattgctggc cctgatgctg caccagacga tccagcacga     2160 tccccctcact accgacctgc gctccagtgc cgaccgctga gcctcctggc ccggaccect     2220 taaaccctgc attccagatg ggggagccgc ccggtgcccg tgtgtccgtt cctccactca     2280
tctgtttctc cggttctccc tgtgcccatc caccggttga ccgcccatct gcctttatca     2340
gagggactgt ccccgtcgac atgttcagtg cctggtgggg ctgcggagtc cactcatcct     2400
tgcctcctct ccctgggttt tgttaataaa attttgaaga aacc                       2444
```

<210> SEQ ID NO 2

<211> LENGTH: 2444
<212> TYPE: DNA
<213> ORGANISM: Homo sapiens

<400> SEQUENCE: 2

| | | | | | |
|---|---|---|---|---|---|
| agatggcggc | gcctgagggg | tcttgggggc | tctaggccgg | ccacctactg | gtttgcagcg | 60 |
| gagacgacgc | atggggcctg | cgcaatagga | gtacgctgcc | tgggaggcgt | gactagaagc | 120 |
| ggaagtagtt | gtgggcgcct | ttgcaaccgc | ctggacgcc | gccgagtggt | ctgtgcaggt | 180 |
| tcgcgggtcg | ctggcggggg | tcgtgaggga | gtgcgccggg | agcggagata | tggagggaga | 240 |
| tggttcagac | ccagagcctc | cagatgccgg | ggaggacagc | aagtccgaga | atggggagaa | 300 |
| tgcgcccatc | tactgcatct | gccgcaaacc | ggacatcaac | tgcttcatga | tcgggtgtga | 360 |
| caactgcaat | gagtggttcc | atggggactg | catccggatc | actgagaaga | tggccaaggc | 420 |
| catccgggag | tggtactgtc | gggagtgcag | agagaaagac | cccaagctag | agattcgcta | 480 |
| tcggcacaag | aagtcacggg | agcgggatgg | caatgagcgg | gacagcagtg | agccccggga | 540 |
| tgagggtgga | gggcgcaaga | ggcctgtccc | tgatccagac | ctgcagcgcc | gggcagggtc | 600 |
| agggacaggg | gttggggcca | tgcttgctcg | ggctctgct | tcgccccaca | aatcctctcc | 660 |
| gcagccttg | gtggccacac | ccagccagca | tcaccagcag | cagcagcagc | agatcaaacg | 720 |
| gtcagcccgc | atgtgtggtg | agtgtgaggc | atgtcggcgc | actgaggact | gtggtcactg | 780 |
| tgatttctgt | cgggacatga | agaagttcgg | ggccccaac | aagatccggc | agaagtgccg | 840 |
| gctgcgccag | tgccgctgc | gggccccggga | atcgtacaag | tacttcccctt | cctcgctctc | 900 |
| accagtgacg | ccctcagagt | ccctgccaag | gccccgccgg | ccactgccca | cccaacagca | 960 |
| gccacagcca | tcacagaagt | tagggcgcat | ccgtgaagat | gaggggggcag | tggcgtcatc | 1020 |
| aacagtcaag | gagcctcctg | aggctacagc | cacacctgag | ccactctcag | atgaggacct | 1080 |
| acctctggat | cctgacctgt | atcaggactt | ctgtgcaggg | gcctttgatg | accatggcct | 1140 |
| gccctggatg | agcgacacag | aagagtcccc | attcctggac | cccgcgctgc | ggaagagggc | 1200 |
| agtgaaagtg | aagcatgtga | agcgtcggga | gaagaagtct | gagaagaaga | aggaggagcg | 1260 |
| atacaagcgg | catcggcaga | agcagaagca | caaggataaa | tggaaacacc | cagagagggc | 1320 |
| tgatgccaag | gaccctgcgt | cactgcccca | gtgcctgggg | cccggctgtg | tgcgccccgc | 1380 |
| ccagcccagc | tccaagtatt | gctcagatga | ctgtggcatg | aagctggcag | ccaaccgcat | 1440 |
| ctacgagatc | ctcccccagc | gcatccagca | gtggcagcag | agcccttgca | ttgctgaaga | 1500 |
| gcacggcaag | aagctgctcg | aacgcattcg | ccgagagcag | cagagtgccc | gcactcgcct | 1560 |
| tcaggaaatg | gaacgccgat | tccatgagct | tgaggccatc | attctacgtg | ccaagcagca | 1620 |
| ggctgtgcgc | gaggatgagg | agagcaacga | gggtgacagt | gatgacacag | acctgcagat | 1680 |
| cttctgtgtt | tcctgtgggc | accccatcaa | cccacgtgtt | gccttgcgcc | acatggagcg | 1740 |
| ctgctacgcc | aagtatgaga | gccagacgtc | ctttgggtcc | atgtacccca | cacgcattga | 1800 |
| aggggccaca | cgactcttct | gtgatgtgta | taatcctcag | agcaaaacat | actgtaagcg | 1860 |
| gctccaggtg | ctgtgcccg | agcactcacg | ggacccaaaa | gtgccagctg | acgaggtatg | 1920 |
| cgggtgcccc | cttgtacgtg | atgtctttga | gctcacgggt | gacttctgcc | gcctgcccaa | 1980 |
| gcgccagtgc | aatcgccatt | actgctggga | gaagctgcgg | cgtgcggaag | tggacttgga | 2040 |
| gcgcgtgcgt | gtgtggtaca | agctggacga | gctgtttgag | caggagcgca | atgtgcgcac | 2100 |
| agccatgaca | aaccgcgcgg | gattgctggc | cctgatgctg | caccagacga | tccagcacga | 2160 |
| tccctcact | accgacctgc | gctccagtgc | cgaccgctga | gcctcctggc | ccggacccct | 2220 |

| | |
|---|---|
| tacaccctgc attccagatg ggggagccgc ccggtgcccg tgtgtccgtt cctccactca | 2280 |
| tctgtttctc cggttctccc tgtgcccatc caccggttga ccgcccatct gcctttatca | 2340 |
| gagggactgt ccccgtcgac atgttcagtg cctggtgggg ctgcggagtc cactcatcct | 2400 |
| tgcctcctct ccctgggttt tgttaataaa attttgaaga aacc | 2444 |

<210> SEQ ID NO 3
<211> LENGTH: 3257
<212> TYPE: DNA
<213> ORGANISM: Homo sapiens

<400> SEQUENCE: 3

| | |
|---|---|
| ccgctgctgc ccctgtggga agggacctcg agtgtgaagc atccttccct gtagctgctg | 60 |
| tccagtctgc ccgccagacc ctctggagaa gccctgcccc ccagcatgg gtttctgccg | 120 |
| cagcgccctg cacccgctgt ctctcctggt gcaggccatc atgctggcca tgaccctggc | 180 |
| cctgggtacc ttgcctgcct tcctaccctg tgagctccag ccccacggcc tggtgaactg | 240 |
| caactggctg ttcctgaagt ctgtgcccca cttctccatg gcagcacccc gtggcaatgt | 300 |
| caccagcctt tccttgtcct ccaaccgcat ccaccacctc catgattctg actttgccca | 360 |
| cctgcccagc ctgcggcatc tcaacctcaa gtggaactgc cgccggttg gcctcagccc | 420 |
| catgcacttc ccctgccaca tgaccatcga gcccagcacc ttcttggctg tgcccaccct | 480 |
| ggaagagcta aacctgagct acaacaacat catgactgtg cctcgcgctgc ccaaatccct | 540 |
| catatccctg tccctcagcc ataccaacat cctgatgcta actctgcca gcctcgccgg | 600 |
| cctgcatgcc ctgcgcttcc tattcatgga cggcaactgt tattacaaga accctgcag | 660 |
| gcaggcactg gaggtggccc cgggtgcccct ccttggcctg gcaacctca cccacctgtc | 720 |
| actcaagtac aacaacctca ctgtggtgcc ccgcaacctg ccttccagcc tggagtatct | 780 |
| gctgttgtcc tacaaccgca tcgtcaaact ggcgcctgag gacctggca atctgaccgc | 840 |
| cctgcgtgtg ctcgatgtgg gcggaaattg ccgccgctgc gaccacgctc ccaacccctg | 900 |
| catggagtgc cctcgtcact tcccccagct acatcccgat accttcagcc acctgagccg | 960 |
| tcttgaaggc ctggtgttga aggacagttc tctctcctgg ctgaatgcca gttggttccg | 1020 |
| tgggctggga aacctccgag tgctggacct gagtgagaac ttcctctaca aatgcatcac | 1080 |
| taaaaccaag gccttccagg gcctaacaca gctgcgcaag cttaacctgt ccttcaatta | 1140 |
| ccaaaagagg gtgtccttg cccacctgtc tctggcccct tccttcggga gcctggtcgc | 1200 |
| cctgaaggag ctggacatgc acggcatctt cttccgctca ctcgatgaga ccacgctccg | 1260 |
| gccactggcc cgcctgccca tgctccagac tctgcgtctg cagatgaact tcatcaacca | 1320 |
| ggcccagctc ggcatcttca gggccttccc tggcctgcgc tacgtggacc tgtcggacaa | 1380 |
| ccgcatcagc ggagcttcgg agctgacagc accatgggg gaggcagatg gagggagaa | 1440 |
| ggtctggctg cagcctgggg accttgctcc ggccccagtg acactccca gctctgaaga | 1500 |
| cttcaggccc aactgcagca ccctcaactt caccttggat ctgtcacgga caacctggt | 1560 |
| gaccgtgcag ccggagatgt ttgcccagct ctcgcacctg cagtgcctgc gcctgagcca | 1620 |
| caactgcatc tcgcaggcag tcaatggctc ccagttcctg ccgctgaccg tctgcaggt | 1680 |
| gctagacctg tcccacaata agctggacct ctaccacgag cactcattca cggagctacc | 1740 |
| acgactggag gccctggacc tcagctacaa cagccagccc tttggcatgc agggcgtggg | 1800 |
| ccacaacttc agcttcgtgg ctcacctgcg caccctgcgc cacctcagcc tggcccacaa | 1860 |
| caacatccac agccaagtgt cccagcagct ctgcagtacg tcgctgcggg ccctggactt | 1920 |

```
cagcggcaat gcactgggcc atatgtgggc cgagggagac ctctatctgc acttcttcca   1980
aggcctgagc ggtttgatct ggctggactt gtcccagaac cgcctgcaca ccctcctgcc   2040
ccaaaccctg cgcaacctcc caagagcct acaggtgctg cgtctccgtg acaattacct    2100
ggccttcttt aagtggtgga gcctccactt cctgcccaaa ctggaagtcc tcgacctggc   2160
aggaaaccag ctgaaggccc tgaccaatgg cagcctgcct gctggcaccc ggctccggag   2220
gctggatgtc agctgcaaca gcatcagctt cgtggccccc ggcttctttt ccaaggccaa   2280
ggagctgcga gagctcaacc ttagcgccaa cgccctcaag acagtggacc actcctggtt   2340
tgggcccctg gcgagtgccc tgcaaatact agatgtaagc gccaaccctc tgcactgcgc   2400
ctgtggggcg gcctttatgg acttcctgct ggaggtgcag gctgccgtgc ccggtctgcc   2460
cagccgggtg aagtgtggca gtccgggcca gctccagggc tcagcatct ttgcacagga    2520 cctgcgcctc tgcctggatg aggccctctc ctgggactgt ttcgccctct cgctgctggc   2580
tgtggctctg ggcctgggtg tgcccatgct gcatcacctc tgtggctggg acctctggta   2640
ctgcttccac ctgtgcctgg cctggcttcc ctggcggggg cggcaaagtg ggcgagatga   2700
ggatgccctg ccctacgatg ccttcgtggt cttcgacaaa acgcagagcg cagtggcaga   2760
ctgggtgtac aacgagcttc gggggcagct ggaggagtgc cgtgggcgct gggcactccg   2820
cctgtgcctg gaggaacgcg actggctgcc tggcaaaacc ctctttgaga acctgtgggc   2880
ctcggtctat ggcagccgca agacgctgtt tgtgctggcc cacacggacc gggtcagtgg   2940
tctcttgcgc gccagcttcc tgctggccca gcagcgcctg ctggaggacc gcaaggacgt   3000
cgtggtgctg gtgatcctga gccctgacgg ccgccgctcc cgctacgtgc ggctgcgcca   3060
gcgcctctgc cgccagagtg tcctcctctg gccccaccag cccagtggtc agcgcagctt   3120
ctgggcccag ctgggcatgg ccctgaccag ggacaaccac cacttctata accggaactt   3180
ctgccaggga cccacggccg aatagccgtg agccggaatc ctgcacggtg ccacctccac   3240
actcacctca cctctgc                                                  3257

<210> SEQ ID NO 4
<211> LENGTH: 3110
<212> TYPE: DNA
<213> ORGANISM: Homo sapiens

<400> SEQUENCE: 4
tggtgaactg caactggctg ttcctgaagt ctgtgcccca cttctccatg cagcacccc     60 gtggcaatgt caccagcctt ccttgtcct ccaaccgcat ccaccactc catgattctg     120 actttgccca cctgcccagc ctgcggcatc tcaacctcaa gtggaactgc ccgccggttg    180
gcctcagccc catgcactt ccctgccaca tgaccatcga gccagcacc ttcttggctg     240 tgcccaccct ggaagagcta aacctgagct acaacaacat catgactgtg cctgcgctgc    300
ccaaatccct catatccctg tccctcagcc ataccaacat cctgatgcta gactctgcca    360
gcctcgccgg cctgcatgcc ctgcgcttcc tattcatgga cggcaactgt tattacaaga    420 accccctgcag gcaggcactg gaggtggccc cgggtgccct ccttggcctg gcaaccctca    480
cccacctgtc actcaagtac aacaacctca ctgtggtgcc ccgcaacctg ccttccagcc    540
tggagtatct gctgttgtcc tacaaccgca tcgtcaaact ggcgcctgag gacctggcca    600
atctgaccgc cctgcgtgtg ctcgatgtgg gcggaaattg ccggccgctg caccacgctc    660
ccaacccctg catggagtgc cctcgtcact tcccccagct acatcccgat ccttcagcc     720 acctgagccg tcttgaaggc ctggtgttga aggacagttc tctctcctgg ctgaatgcca    780
```

-continued

| | | |
|---|---|---|
| gttggttccg tgggctggga aacctccgag tgctggacct gagtgagaac ttcctctaca | 840 | |
| aatgcatcac taaaaccaag gccttccagg gcctaacaca gctgcgcaag cttaacctgt | 900 | |
| ccttcaatta ccaaaagagg gtgtcctttg cccacctgtc tctggcccct ccttcgggaa | 960 | |
| gcctggtcgc cctgaaggag ctggacatgc acggcatctt cttccgctca ctcgatgaga | 1020 | |
| ccacgctccg gccactggcc cgcctgccca tgctccagac tctgcgtctg cagatgaact | 1080 | |
| tcatcaacca ggcccagctc ggcatcttca gggccttccc tggcctgcgc tacgtggacc | 1140 | |
| tgtcggacaa ccgcatcagc ggagcttcgg agctgacagc caccatgggg gaggcagatg | 1200 | |
| gaggggagaa ggtctggctg cagcctgggg accttgctcc ggccccagtg acactccca | 1260 | |
| gctctgaaga cttcaggccc aactgcagca ccctcaactt caccttggat ctgtcacgga | 1320 | |
| acaacctggt gaccgtgcag ccggagatgt tgcccagctc tcgcacctg cagtgcctgc | 1380 | |
| gcctgagcca caactgcatc tcgcaggcag tcaatggctc ccagttcctg ccgctgaccg | 1440 | |
| gtctgcaggt gctagacctg tcccacaata agctggaccet ctaccacgag cactcattca | 1500 | |
| cggagctacc acgactggag gccctggacc tcagctacaa cagccagccc tttggcatgc | 1560 | |
| agggcgtggg ccacaacttc agcttcgtgg ctcacctgcg caccctgcgc cacctcagcc | 1620 | |
| tggcccacaa caacatccac agccaagtgt cccagcagct ctgcagtacg tcgctgcggg | 1680 | |
| ccctggactt cagcggcaat gcactgggcc atatgtgggc cgagggagac ctctatctgc | 1740 | |
| acttcttcca aggcctgagc ggtttgatct ggctggactt gtcccagaac cgcctgcaca | 1800 | |
| ccctcctgcc ccaaaccctg cgcaacctcc ccaagagcct acaggtgctg cgtctccgtg | 1860 | |
| acaattacct ggccttcttt aagtggtgga gcctccactt cctgcccaaa ctggaagtcc | 1920 | |
| tcgacctggc aggaaaccag ctgaaggccc tgaccaatgg cagcctgcct gctggcaccc | 1980 | |
| ggctccggag gctggatgtc agctgcaaca gcatcagctt cgtggccccc ggcttctttt | 2040 | |
| ccaaggccaa ggagctgcga gagctcaacc ttagcgccaa cgccctcaag acagtggacc | 2100 | |
| actcctggtt tgggcccctg gcgagtgccc tgcaaatact agatgtaagc gccaaccctc | 2160 | |
| tgcactgcgc ctgtgggcg gccttttatg acttcctgct ggaggtgcag gctgccgtgc | 2220 | |
| ccggtctgcc cagccgggtg aagtgtggca gtccgggcca gctccagggc ctcagcatct | 2280 | |
| ttgcacagga cctgcgcctc tgcctggatg aggccctctc ctgggactgt ttcgccctct | 2340 | |
| cgctgctggc tgtggctctg ggcctgggtg tgccatgct gcatcacctc tgtggctggg | 2400 | |
| acctctggta ctgcttccac ctgtgcctgg cctggcttcc ctggcggggg cggcaaagtg | 2460 | |
| ggcgagatga ggatgccctg ccctacgatg ccttcgtggt cttcgacaaa acgcagagcg | 2520 | |
| cagtggcaga ctgggtgtac aacgagcttc gggggcagct ggaggagtgc cgtgggcgct | 2580 | |
| gggcactccg cctgtgcctg gaggaacgcg actggctgcc tggcaaaacc ctctttgaga | 2640 | |
| acctgtgggc ctcggtctat ggcagccgca agacgctgtt tgtgctggcc cacacggacc | 2700 | |
| gggtcagtgg tctcttgcgc gccagcttcc tgctggccca gcagccctg ctggaggacc | 2760 | |
| gcaaggacgt cgtggtgctg gtgatcctga gccctgacgg ccgccgctcc cgctatgtgc | 2820 | |
| ggctgcgcca gcgcctctgc cgccagagtg tcctcctctg gccccaccag ccagtggtc | 2880 | |
| agcgcagctt ctgggcccag ctgggcatgg ccctgaccag ggacaaccac cacttctata | 2940 | |
| accggaactt ctgccaggga cccacggccg aatagccgtg agccggaatc ctgcacggtg | 3000 | |
| ccacctccac actcacctca cctctgcctg cctggtctga ccctcccctg ctcgcctccc | 3060 | |
| tcaccccaca cctgacacag agcaggcact caataaatgc taccgaaggc | 3110 | |

<210> SEQ ID NO 5

<211> LENGTH: 3868
<212> TYPE: DNA
<213> ORGANISM: Homo sapiens

<400> SEQUENCE: 5

| | | | | | | |
|---|---|---|---|---|---|---|
| ggaggtcttg | tttccggaag | atgttgcaag | gctgtggtga | aggcaggtgc | agcctagcct | 60 |
| cctgctcaag | ctacaccctg | gccctccacg | catgaggccc | tgcagaactc | tggagatggt | 120 |
| gcctacaagg | gcagaaaagg | acaagtcggc | agccgctgtc | ctgagggcac | cagctgtggt | 180 |
| gcaggagcca | agacctgagg | gtggaagtgt | cctcttagaa | tggggagtgc | ccagcaaggt | 240 |
| gtacccgcta | ctggtgctat | ccagaattcc | catctctccc | tgctctctgc | ctgagctctg | 300 |
| ggccttagct | cctccctggg | cttggtagag | acaggtgtg | aggccctcat | gggatgtagg | 360 |
| ctgtctgaga | ggggagtgga | aagaggaagg | ggtgaaggag | ctgtctgcca | tttgactatg | 420 |
| caaatggcct | ttgactcatg | ggaccctgtc | ctcctcactg | ggggcagggt | ggagtggagg | 480 |
| gggagctact | aggctggtat | aaaaatctta | cttcctctat | tctctgagcc | gctgctgccc | 540 |
| ctgtgggaag | ggacctcgag | tgtgaagcat | ccttccctgt | agctgctgtc | cagtctgccc | 600 |
| gccagaccct | ctggagaagc | ccctgccccc | cagcatggg | ttctgccgca | gcgccctgca | 660 |
| cccgctgtct | ctcctggtgc | aggccatcat | gctggccatg | accctggccc | tgggtacctt | 720 |
| gcctgccttc | ctaccctgtg | agctccagcc | ccacggcctg | gtgaactgca | actggctgtt | 780 |
| cctgaagtct | gtgccccact | tctccatggc | agcaccccgt | ggcaatgtca | ccagcctttc | 840 |
| cttgtcctcc | aaccgcatcc | accacctcca | tgattctgac | tttgcccacc | tgcccagcct | 900 |
| gcggcatctc | aacctcaagt | ggaactgccc | gccggttggc | ctcagcccca | tgcacttccc | 960 |
| ctgcccacatg | accatcgagc | ccagcacctt | cttggctgtg | cccaccctgg | aagagctaaa | 1020 |
| cctgagctac | aacaacatca | tgactgtgcc | tcgcgctgcc | caaatccctca | tatccctgtc | 1080 |
| cctcagccat | accaacatcc | tgatgctaga | ctctgccagc | ctcgccggcc | tgcatgccct | 1140 |
| gcgcttccta | ttcatggacg | gcaactgtta | ttacaagaac | ccctgcaggc | aggcactgga | 1200 |
| ggtggccccg | ggtgccctcc | ttggcctggg | caacctcacc | cacctgtcac | tcaagtacaa | 1260 |
| caacctcact | gtggtgcccc | gcaacctgcc | ttccagcctg | gagtatctgc | tgttgtccta | 1320 |
| caaccgcatc | gtcaaactgg | cgcctgagga | cctggccaat | ctgaccgccc | tgcgtgtgct | 1380 |
| cgatgtgggc | ggaaattgcc | gccgctgcga | ccacgctccc | aaccctgca | tggagtgccc | 1440 |
| tcgtcacttc | ccccagctac | atcccgatac | cttcagccac | ctgagccgtc | ttgaaggcct | 1500 |
| ggtgttgaag | gacagttctc | tctcctggct | gaatgccagt | tggttccgtg | ggctgggaaa | 1560 |
| cctccgagtg | ctggacctga | gtgagaactt | cctctacaaa | tgcatcacta | aaaccaaggc | 1620 |
| cttccagggc | ctaacacagc | tgcgcaagct | taacctgtcc | ttcaattacc | aaaagagggt | 1680 |
| gtcctttgcc | cacctgtctc | tggccccttc | cttcgggagc | ctggtcgccc | tgaaggagct | 1740 |
| ggacatgcac | ggcatcttct | tccgctcact | cgatgagacc | acgctccggc | cactggcccg | 1800 |
| cctgcccatg | ctccagactc | tgcgtctgca | gatgaacttc | atcaaccagg | cccagctcgg | 1860 |
| catcttcagg | gccttccctg | gcctgcgcta | cgtggacctg | tcggacaacc | gcatcagcgg | 1920 |
| agcttcggag | ctgacagcca | ccatggggga | ggcagatgga | ggggagaagg | tctggctgca | 1980 |
| gcctgggac | cttgctccgg | ccccagtgga | cactcccagc | tctgaagact | tcaggcccaa | 2040 |
| ctgcagcacc | ctcaacttca | ccttggatct | gtcacggaac | aacctggtga | ccgtgcagcc | 2100 |
| ggagatgttt | gcccagctct | cgcacctgca | gtgcctgcgc | ctgagccaca | actgcatctc | 2160 |
| gcaggcagtc | aatggctccc | agttcctgcc | gctgaccggt | ctgcaggtgc | tagacctgtc | 2220 |

-continued

```
ccacaataag ctggacctct accacgagca ctcattcacg agctaccac gactggaggc    2280 cctggacctc agctacaaca gccagccctt tggcatgcag ggcgtgggcc acaacttcag    2340
cttcgtggct cacctgcgca ccctgcgcca cctcagcctg gcccacaaca acatccacag    2400
ccaagtgtcc cagcagctct gcagtacgtc gctgcgggcc ctggacttca gcggcaatgc    2460
actgggccat atgtgggccg agggagacct ctatctgcac ttcttccaag gcctgagcgg    2520
tttgatctgg ctggacttgt cccagaaccg cctgcacacc ctcctgcccc aaaccctgcg    2580
caacctcccc aagagcctac aggtgctgcg tctccgtgac aattacctgg ccttctttaa    2640
gtggtggagc ctccacttcc tgcccaaact ggaagtcctc gacctggcag aaaccagct     2700 gaaggccctg accaatggca gcctgcctgc tggcacccgg ctccggaggc tggatgtcag    2760
ctgcaacagc atcagcttcg tggccccggg cttcttttcc aaggccaagg agctgcgaga    2820
gctcaacctt agcgccaacg ccctcaagac agtggaccac tcctggtttg gcccctggc     2880 gagtgccctg caaatactag atgtaagcgc caaccctctg cactgcgcct gtggggcggc    2940
ctttatggac ttcctgctgg aggtgcaggc tgccgtgccc ggtctgccca gccgggtgaa    3000
gtgtggcagt ccgggccagc tccagggcct cagcatcttt gcacaggacc tgcgcctctg    3060
cctggatgag gccctctcct gggactgttt cgccctctcg ctgctggctg tggctctggg    3120
cctgggtgtg cccatgctgc atcacctctg tggctgggac ctctggtact gcttccacct    3180
gtgcctggcc tggcttccct ggcgggggcg gcaaagtggg cgagatgagg atgccctgcc    3240
ctacgatgcc ttcgtggtct tcgacaaaac gcagagcgca gtggcagact gggtgtacaa    3300
cgagcttcgg gggcagctgg aggagtgccg tgggcgctgg gcactccgcc tgtgcctgga    3360
ggaacgcgac tggctgcctg gcaaaaccct ctttgagaac ctgtgggcct cggtctatgg    3420
cagccgcaag acgctgtttg tgctggccca cacggaccgg gtcagtggtc tcttgcgcgc    3480
cagcttcctg ctggcccagc agcgcctgct ggaggaccgc aaggacgtcg tggtgctggt    3540
gatcctgagc cctgacggcc gccgctcccg ctatgtgcgg ctgcgccagc gcctctgccg    3600
ccagagtgtc ctcctctggc cccaccagcc cagtggtcag cgcagcttct gggcccagct    3660
gggcatggcc ctgaccaggg acaaccacca cttctataac cggaacttct gccagggacc    3720
cacggccgaa tagccgtgag ccggaatcct gcacggtgcc acctccacac tcacctcacc    3780
tctgcctgcc tggtctgacc ctcccctgct cgcctccctc accccacacc tgacacagag    3840
caggcactca ataaatgcta ccgaaggc                                       3868
```

<210> SEQ ID NO 6
<211> LENGTH: 26
<212> TYPE: DNA
<213> ORGANISM: Homo sapiens

<400> SEQUENCE: 6
agcatacaag caaatttttt acaccg                                          26

<210> SEQ ID NO 7
<211> LENGTH: 24
<212> TYPE: DNA
<213> ORGANISM: Homo sapiens

<400> SEQUENCE: 7
gttctgttat tgacacccgc aatt                                            24

<210> SEQ ID NO 8
<211> LENGTH: 24
<212> TYPE: DNA

```
<213> ORGANISM: Homo sapiens

<400> SEQUENCE: 8
ccttcctaat aatcctgcgg atgt                                            24

<210> SEQ ID NO 9
<211> LENGTH: 28
<212> TYPE: DNA
<213> ORGANISM: Homo sapiens

<400> SEQUENCE: 9
ctgaaggtag cattagtctt tgataacg                                        28
```